United States Patent [19]

Higashi et al.

[11] Patent Number: 5,049,156
[45] Date of Patent: Sep. 17, 1991

[54] INTRA-OCULAR LENS

[75] Inventors: Kazumi Higashi; Kazuhide Fujita; Yoshinori Yoshida; Kiichiro Matsushita, all of Osaka; Kazuhiko Nakada, Aichi, all of Japan

[73] Assignees: Nitto Denko Corporation, Osaka; Menicon Co., Ltd., Aichi, both of Japan

[21] Appl. No.: 604,318

[22] Filed: Oct. 29, 1990

[30] Foreign Application Priority Data

Oct. 30, 1989 [JP] Japan .................................. 1-282541
Sep. 5, 1990 [JP] Japan .................................. 2-236854

[51] Int. Cl.⁵ .............................................. A61F 2/16
[52] U.S. Cl. ...................................................... 623/6
[58] Field of Search ...................................... 623/4–6; 528/185

[56] References Cited

U.S. PATENT DOCUMENTS

| | | | |
|---|---|---|---|
| 3,959,350 | 5/1976 | Rogers | 528/185 |
| 4,450,593 | 5/1984 | Poler | 623/6 |
| 4,601,720 | 2/1986 | Sinskey | 623/6 |
| 4,612,361 | 9/1986 | Peters | 528/185 |
| 4,725,277 | 2/1988 | Bissonette | 623/6 |
| 4,955,900 | 9/1990 | Higashi et al. | 623/6 |

Primary Examiner—Ronald Frinks
Attorney, Agent, or Firm—Sughrue, Mion, Zinn, Macpeak & Seas

[57] ABSTRACT

An intra-ocular lens comprising a lens part and a fixing part for fixing the lens part in an eye, the lens part comprising a colorless and transparent polyimide containing at least one of repeating units represented by formulae (I) to (IV):

(I)

(II)

(III)

(Abstract continued on next page.)

-continued (IV)

wherein
X₁ represents $-\underset{\underset{CH_3}{|}}{\overset{\overset{CH_3}{|}}{C}}-$, $-SO_2-$, $-\underset{\underset{CF_3}{|}}{\overset{\overset{CF_3}{|}}{C}}-$ or $-O-$;

X₂ represents and

X₃ represents $-\underset{\underset{CH_3}{|}}{\overset{\overset{CH_3}{|}}{C}}-$, $-SO_2-$ or $-\underset{\underset{CF_3}{|}}{\overset{\overset{CF_3}{|}}{C}}-$.

Further, the lens part and the fixing part may be integrally molded together, if desired.

4 Claims, 2 Drawing Sheets

INTRA-OCULAR LENS

FIELD OF THE INVENTION

The present invention relates to an intra-ocular lens (artificial crystalline lens) which can be implanted in the anterior chamber or the posterior chamber of an eye of a person suffering from aphakia after the extraction of crystalline lens for treating, for example, cataract to thereby enable the recovery of the eyesight.

BACKGROUND OF THE INVENTION

Conventional method for the recovery of the eyesight (refraction) of a patient of aphakia caused by the extraction of crystalline lens for treating, for example, cataract include correction with glasses, the use of contact lenses and the transplantation of intra-ocular lenses.

Although the correction with glasses enables the recovery of the eyesight after the operation, this method is accompanied by some troubles such as the constriction of visual field (enlargement of retinal image) and a so-called Jack-in-the-box phenomenon. In order to use glasses in practice, therefore, a certain period of time for training is required. In the case of hemiaphakia, in particular, aniseikonia makes it impossible to achieve binocular functions.

Contact lenses are effective on such aniseikonia. Recently soft contact lenses of a high moisture content, which can be continuously worn, have been developed and thus the aforesaid problem is now being settled. For many aged patients, however, it is difficult to handle contact lenses. Thus there are few patients who wear contact lenses provided after the operation in practice.

Accordingly, it seems that correction of eyesight with glasses or contact lenses is not preferable.

On the other hand, the transplantation of artificial crystalline lens (i.e., an intra-ocular lens), which has been performed for these 30 years, is superior in various points, for example, showing less enlargement of retinal image, never accompanied by constriction of visual field or annular scotoma, achieving binocular functions, which is advantageous compared with glasses, in particular, in the case of hemiaphakia, requiring no training time, requiring no handling, once transplanted. Owing to recent progress in microscopes and ultrasonic knives, transplantation techniques have been improved. Further, the material and shape of intra-ocular lenses have been improved. Thus it is expected that the aforesaid intra-ocular lenses will become the most important method for the correction of eyesight of patients of aphakia.

Thus, an intra-ocular lens shows an excellent effect of correcting eyesight. However, it is a foreign matter in an eye and thus suffers from the problem of ophthalmicus complicating diseases. It is sometimes observed that the transplantation of an intra-ocular lens causes corneal endothelium disorders followed by decompensation, which finally results in blindness. Therefore, an intra-ocular lens should be made of a material which shows no biotoxicity and a high biocompatibility and is never modified or deteriorated in a living organism.

Natural light involves rays falling within the ultraviolet, visible and infrared wavelength regions. There is a fear that the penetration of a large amount of ultraviolet rays through an eye might induce retinal disorders. The crystalline lens of an eye further plays a role of predominantly absorbing the ultraviolet rays so as to protect the retina. Thus, the transmission of ultraviolet rays is a serious problem in the aforesaid aphakial eyes. Therefore, it is required that the material of the aforesaid intra-ocular lens would absorb ultraviolet rays falling within a wavelength range of from 200 to 380 nm and remain transparent for visible rays falling within a wavelength range of from 380 to 780 nm. It is furthermore desired that the material essentially has such a small specific gravity as to lighten a burden of the eye as well as such a high refraction index as to minimize the thickness of the lens.

Polymethyl methacrylate (PMMA), which is now the most frequently employed for intra-ocular lenses, is excellent in optical properties, highly resistant against acids, alkalis and organic solvents and scarcely shows any change with the lapse of time.

However, PMMA shows a low heat stability (i.e., a glass transition temperature (Tg) of 105° C. or lower), which makes it impossible to sterilize PMMA with a steam autoclave. That is, autoclave sterilization is usually performed at 121° C. under 1.2 atmosphere for 1 hour. Under such conditions, PMMA would be softened and deformed, which makes it unavailable. Thus, an intra-ocular lens made of PMMA is sterilized with the use of, for example, ethylene oxide gas. In this case, however, it is liable that the gas remaining in the lens would induce inflammation on a mucosa, when the intra-ocular lens is put into an eye. Thus, the aforesaid gas sterilization method necessarily involves a degassing step. This step requires approximately 2 weeks, which results in an increase in the cost. As a result, intraocular lenses sterilized by this method are generally more expensive than those subjected to steam sterilization. In addition, PMMA transmits a substantial amount of ultraviolet rays, which causes another problem of the damage of the retina with ultraviolet rays, as described above. In order to solve this problem, an UV absorber to PMMA is proposed, as described in JP-A-60-232149. (The term "JP-A" as used herein means an "unexamined published Japanese patent application"). However this method is not a preferable one, since the addition of an UV absorber would deteriorate the transmittance of visible rays. Further, there is a fear that the UV absorber thus added might slowly ooze out from the lens and thus exert undesirable effects to an organism. In addition, the aforesaid PMMA has a lower refraction index (approximately 1.49) than that of glass. Thus there is a possibility that the lens would adhere to the iris and thus cause complicating diseases.

As described above, PMMA has a number of disadvantages, though it is advantageous in many points. Thus, attempts have been made to develop a material which can be sterilized in an autoclave, absorb ultraviolet rays and has a high refraction index. For example, glass, which has a high refraction index and can absorb ultraviolet rays, is difficult to process. Further, it has a large specific gravity (2.5) and thus a lens made of glass is heavy per se, which causes a serious burden on an eye. Thus glass is not suitable as a material for an intra-ocular lens. Natural and synthetic crystalline materials, for example, sapphire, ruby, corundum, silicon, diamond can also absorb ultraviolet rays. However, these materials are unsuitable as a material for intra-ocular lenses, since it is difficult to process them and each of them has a large specific gravity, similar to glass. Recently, therefore, synthetic resins capable of substituting for PMMA have attracted public attention and attempts have been made to utilize, for example, polysulfone, polyarylate, polyether imide therefor. The above-mentioned polysulfone has a high refraction index, can absorb ultraviolet rays and shows a softening point of 175° C. which enables autoclave sterilization. However the poor processability of polysulfone makes the practical use thereof impossible. Polyarylate has a high refraction index, can absorb ultraviolet rays and can be sterilized in an autoclave. However, the poor processability of polyarylate prevents the practical application thereof, similar to the case of the above-mentioned polysulfone. On the other hand, polyether imide is excellent not only in refraction index, ultraviolet ray absorptivity and autoclave sterilization properties but also in processability. However, this resin has a yellow or yellowish brown color, which restricts the transmission of visible rays. Thus, it is impossible to use polyether imide as an intra-ocular lens.

Namely, although PMMA has such disadvantages as described above, no material substituting therefor has been found out so far. Thus, PMMA, which has been sterilized by the aforesaid expensive gas sterilization method and contains an UV absorber which might exert some undesirable effects on living organisms, is employed as a material for intra-ocular lenses at present.

Therefore, it has been urgently required to develop an intra-ocular lens material which can be easily processed into a thin lens by, for example, mechanical processing or molding, has a specific gravity of 1.7 or less, preferably 1.5 or less, and a refraction index of 1.5 or more, preferably 1.6 or more, is chemically stable and biologically compatible, can absorb ultraviolet rays which is dangerous to the retina and has such a high heat resistance as to withstand autoclave sterilization.

SUMMARY OF THE INVENTION

An object of the present invention is to provided an intra-ocular lens exhibiting an excellent biocompatibility, a high ultraviolet ray absorptivity, such a small specific gravity as specified above and such a high heat resistance as to withstand autoclave sterilization.

Other objects and effects of the present invention will be apparent from the following description.

The present invention relates to an intra-ocular lens comprising a lens part and a fixing part for fixing the lens part in an eye, the lens part comprising a colorless and transparent polyimide containing at least one of repeating units represented by formulae (I) to (IV):

(I)

(II)

(III)

(IV)

wherein $X_1$ represents $X_2$ represents

; and $X_3$ represents

DETAILED DESCRIPTION OF THE INVENTION

Accordingly, the present inventors have conducted extensive studies in order to develop an intra-ocular lens superior to the aforesaid PMMA lens and examined a series of resins. As a result, they have found out that an aromatic polyimide is superior to PMMA in properties since it can completely absorb ultraviolet rays, has a high refraction index (1.6 or above) and shows a sufficient heat resistance for performing autoclave sterilization. However, an aromatic polyimide has a yellow or brown color and thus absorbs not only visible rays but also a substantial part of visible rays. Therefore, the present inventors have conducted studies in order to develop an aromatic polyimide which would never absorb visible rays. As a result, it has been found that an aromatic polyimide comprising at least one of repeating units represented by formulae (I) to (IV) as the main component can completely absorb ultraviolet rays but most of visible rays can transmit therethrough, thus giving a substantially transparent intra-ocular lens; and that the polyimide has various properties required for an intra-ocular lens material, similar to conventional aromatic polyimides, and a high biocompatibility, thus achieving the present invention.

Namely, the intra-ocular lens of the present invention comprises a lens part comprising a colorless and transparent polyimide containing at least one of repeating units represented by formulae (I) to (IV) as the main component which is biologically compatible and chemically inactive, suffers from neither modification nor deterioration in a living organism, has a refraction index of 1.6 romore, can completely absorb ultraviolet rays falling within a wavelength region of 200 to 380 nm, is substantially transparent for visible rays falling within a wavelength range of 380 to 780 nm and has such as high heat resistance as to withstand autoclave sterilization.

The intra-ocular lens of the present invention comprises a lens part and a fixing part for fixing the lens part in an eye. The lens part, which is optionally integrally moled together with the fixing part, comprises a colorless and transparent polyimide containing at least one of relating units represented by formulae (I) to (IV) as the main component.

Such a colorless and transparent polyimide may be obtained by, for example, reacting 4,4'-oxydiphthalic dianhydride represented by formula (V):

(V)

with aromatic diamino compounds represented by formulae (VI) to (IX). These aromatic diamino compounds of formulae (VI) to (IX) respectively correspond to the compounds of formulae (I) to (IV):

(VI)

(VII)

(VIII)

(IX)

wherein
$X_1$ represents

$X_2$ represents

; and

$X_3$ represents

Specific examples of the aforesaid aromatic diamino compounds include:
2,2-bis(4-(4-aminophenoxy)phenyl)propane;

bis(4-(4-aminophenoxxy)pehnyl)sulfone;

2,2-bis(4-(4-aminophenoxxy)phenyl)hexafluoropropane;

1,3-bis(4-aminophenoxy)benezene;

1,4-bixs(4-aminophenoxy)benzene;

4,4'-bxis(aminophenoxy)biphenyl

4,4'-diaminodiphenylpropane;

4'-diaminodiphenylhexafluoropropane;

(4-(3-aminophenoxxy)phenyl)sulfone;

2,2-bis(4-(3-aminophenoxy)phenyl)propane;

2,2-bis(4-(3-aminophenoxxy)phenyl)hexxafluoropropane;

3,3'-diaminophenylsulfone;

3,3'-diaminodiphenylpropane;

3,3'-diaminodiphenylhexafluoropropane;

3,3'-diaminodiphenyl ether;

bis(4-(4-aminophenoxy)peenyl) ether; and 3,4'-diaminodiphenyl either

Either one of these diamino compounds or a mixture thereof may be used.

Thus, the color less and transparent polyimide containing at least one of the repeating units represented by formulae (I) to (IV) as the major component may be obtained by using the aforesaid 4,4'-oxxydiphthalic dianhydride together with the aromatic diamino compound(s). Furthermore, one of the aforesaid aromatic diamino compounds is reacted with the aforesaid 4,4'-oxxydiphthalic dianhydride to thereby give a polyamide acid. Next, this polyamide acid is blended with another polyamide acid prepared by reacting another one of the aforesaid aromatic diamino compound with the foresaid 4,4,'- oxydiphthalic dianhydride. Thus a colorless and transparent polyimide containing at least one of the repeating units represented by formulae (I) to (IV) as the major component may be obtained.

The expression "containing as the major component" as used herein involves a case wherein the polyimide exclusively contains the major component. In this case, the colorless characteristics and transparency of the obtained polyimide would be enhanced with an increase in the content of the repeating units of formulae (I) to (IV).

However, the UV ray-absorptivity and visible ray-transmittance required in the present invention can be secured when the polyimide contains at least 80% by mole of the repeating unit(s) of formulae (I) to (IV). Therefore, the polyimide may contain other aromatic tetracarboxylic dianhydrides other than the aforesaid 4,4,'-oxydiphthalic dianhydride as well as diamino compounds other than the aforesaid aromatic diamino compounds within the range as specified above. Therefore, the content of the repeating unit(s) represented by formulae (I) to (IV) is preferably 80% by mole or more and more preferably 95% by mole or more.

Examples of the aforesaid other aromatic tetracarboxylic dianhydrides include pyromellitic dianhydride, 3,3',4,4,'-biphenyltetarcarbxylic dianhydride, 3,3',4,4,'-benzophenone tetracarboxylic dianhydride, 4,4,'-bis(3,4-dicarboxyphenoxy)diphenylsulfone dianhydride, 2,3,6,7-naphthalene tetracarboxylic dianhydride, 1,2,5,6-naphthalene tetracarboxylic dianhydride, 1,4,5,8-naphthalene tetracarboxylic dianhydride and 1,4,5,8-naphthalene tetracarboxylic dianhydride. Either one of these compounds or a mixture thereof may be employed.

Examples of the aforesaid other diamino compounds include 4,4,'-diaminodiphenyl ether, 4,4,'-diaminodiphenylmethane, 4,4,'-diaminobenzophenone, p-phenylenediamine, benzidine, 3,3,'-dimethylbenzine, 4,4,'-diaminodiphenyl the other and 3,3,'-dimethoxy-4,4,'-diaminodiphenylmethane. Either one of these compounds or a mixture thereof may be employed.

The colorless and transparent polyimide to be used as a material of the intra-ocular lens of the present invention may be obtained, for example, in the following manner. The aforesaid aromatic tetracarboxylic dianhydride is polymerized with the aromatic diamino compound in an organic polar solvent at a temperature of 80° C. or below to thereby give a polyamide acid. Then this polyamide acid is formulated into a desired shape. Then the organic solvent in the shaped article is distilled off in the atmosphere or in an inert gas at a temperature of from 50 to 350° C. under atmospheric or reduced pressure. Simultaneously, the polyamide acid is subjected to dehydration and ring closure to thereby give the target polyimide. Alternately, the polyimide may be obtained by a chemical imitation method. For example, the aforesaid polyamide acid is subjected to desolvation and converted into an imide by using, for example, a solution of pyridine and acetic anhydride in benzene to thereby give a polyimide.

In the above method, the polyamide acid may be isolated by reprecipitation and then subjected to dehydration and ring closure by heating or using a chemical imitation agent to thereby give the target polyimide. It is possible, furthermore, that the reaction mixture after the formation of the polyamide acid is heated to 100° C. or above as such to thereby convert the polyamide acid into an imide. Then the target polyimide may be obtained from the reaction mixture as the precipitate. In this case wherein filtration and washing steps are required, a colorless and transparent polyimide substantially the same as the one obtained above can be prepared.

As the aforesaid organic polar solvent, amide organic polar solvent such as N,N-dimethylformamide and N,N-dimethylacetamide may be preferably employed. It is particularly preferable to use an organic polar solvent having a boiling point of 170° C. or below (for example, N,N-dimethylacetamide). Either one of these organic solvents or a mixture thereof may be used. However, it is preferable not to use N-methyl-2-pyrrolidone as the aforesaid organic polar solvent. This is because N-methyl-2-pyrrolidone would partially decompose upon the heating of the shaped article of the polyamide acid in order to the formation of the polyimide through dehydration and ring closure. Then, the decomposition products of blackish brown color thus formed remain in the product, which causes a yellowish brown coloration of the obtained polyimide. On the other hand, the organic polar solvents as cited above such as N,N-dimethylacetamide have lower boiling points and thus are not decomposed but vaporized during the aforesaid heating step. In this case, therefore, no such coloration as the one described in the case of N-methyl-2-pyrrolidone is observed.

When N-methyl-2-pyrrolidone is used as a polymerization solvent and the polyamide thus formed is reprecipitated by pouring the polyamide acid solution into a poor solvent of the polyamide acid (for example, water) followed by converting the polyamide acid into an imide in the presence of the polymerization solvent or the polyamide acid is redissolved in another preferable solvent followed by converting into an imide, the aforesaid problem accompanied by the use of N-methyl-2-pyrrolidone can be avoided.

The appropriate organic polar solvent as cited above may further contain one or more poor solvents or good solvents which would never damage the transparency (for example, ethanol, toluene, benzene, xylene, dioxane, tetrahydrofuran and nitrobenzene) in such an amount as not to deteriorate the solubility. When these solvents are used in a large amount, however, the solubility of the formed polyamide acid is lowered. Thus, these solvents generally used in an amount of less than 50% by weight, still preferably less than 30% by weight, based on the total solvents.

When the colorless and transparent polyimide is to be produced by the above-mentioned method, the intrinsic viscosity (logarithmic viscosity number) of the polyamide acid solution may preferably range from 0.3 to 5.0, still preferably from 0.4 to 2.0. The intrinsic viscosity is a value determined in N,N-dimethylacetamide at a concentration of 0.5 g/100 ml. When the intrinsic viscosity is excessively low, the obtained intra-ocular lens has a poor mechanical strength. When it is excessively high, on the other hand, it becomes difficult to formulate the polyamide acid solution into a desired shape or to isolate the polyamide acid. From the viewpoint of workability, the concentration of the polyamide acid solution preferably ranges from 5 to 30% by weight, more preferably from 15 to 25% by weight.

The aforesaid intrinsic viscosity may be calculated in accordance with the following equation wherein the viscosity is measured with a capillary tube viscometer.

$$\text{Intrinsic viscosity} = \frac{\text{Natural logarithm} \frac{\text{(Viscosity of solution)}}{\text{(Viscosity of solvent)}}}{\text{Concentration of polymer in solution}}$$

The colorless and transparent polyimide thus obtained may be processed into an intra-ocular lens by, for example, the following methods.

The first method may be performed as follows. The aforesaid polyamide acid solution is casted onto a planished glass or stainless plate in such a manner as to give a homogeneous thickness. Then it is slowly heated to 100 to 350° C. to thereby induce dehydration and ring closure. Thus the polyamide acid is converted into an imide and a polyimide film is formed. In the formation of the film form the polyamide acid solution, the heating for the removal of the organic polar solvent and the imitation of the polyamide acid salt may be continuously carried out. These steps may be performed under reduced pressure or under an inert gas atmosphere. Another method for the formation of a polyimide film may be performed as follows. Namely, the aforesaid polyamide acid solution is casted onto a glass plate and dried by heating to 100 to 150° C. for 30 to 120 minutes. Then the coating thus obtained is immersed in a solution of pyridine and acetic anhydride in benzene to thereby effect desolvation and imitation. Thus the aforesaid coating is converted into a polyimide film. Then the obtained polyimide films thus obtained are laminated in such a manner as to give a molded sheet of a desired thickness and subjected to hot press molding at a temperature of 200 to 400° C. under a pressure of 0.5 to 10 t/cm² for 0.1 to 10 hours. Thus a polyimide molded product having a transparency is obtained. Next, this molded article is abraded with an abrasion device to thereby give an intra-ocular lens.

The second method may be performed as follows. The aforesaid polyamide acid solution is poured into a poor solvent such as water or methanol to thereby reprecipitate the polyamide acid. After recovering, the polyamide acid is subjected to dehydration and ring closure by heating to 100 to 350° C. Subsequently, the imide thus obtained is ground to thereby give a colorless and transparent polyimide powder. This powder is subjected to hot press molding, similar to the first method, at a temperature of 200 to 400° C. under a pressure of 0.5 to 10 t/cm² for 1 to 10 hours. Thus a polyimide molded product having a transparency is obtained. This molded article is then abraded in the same manner as the one described above to thereby give an intra-ocular lens.

In the above second method, the colorless and transparent polyimide powder may be obtained, alternately, by the following procedure. Namely, the polyamide acid solution is heated to 100 to 200° C. under stirring to thereby convert the polyamide acid into polyimide which is then recovered as a precipitate. In this case, the obtained polyimide may be subjected to the hot press molding after simply washing and drying.

When an intra-ocular lens is to be produced from the colorless and transparent polyimide film or polyimide powder obtained above, it is preferable, from the viewpoint of the mechanical strength, that the obtained intra-ocular lens has an intrinsic viscosity (determined in 97% sulfuric acid at a concentration of 0.5 g/dl at 30° C.) of from 0.3 to 4.0, most preferably from 0.4 to 2.0.

The third method may be performed as follows. In this method, a polyimide molded product is directly obtained from the aforesaid polyamide acid solution, without using the hot press molding as done in the first and second methods. In a conventional drying method, it is impossible to inhibit foaming of the material in such a case. Thus a homogeneous polyimide molded product of a thickness of 150 μm or more can be hardly obtained thereby. However, a polyimide molded product of 500 μm or more in thickness suffering from no foaming can be obtained by allowing the polyamide acid solution under reduced pressure for a long time and then internally heating it with the use of far infrared rays or microwave. Namely, a homogeneous polyimide molded product can be obtained directly from the polyamide acid by using far infrared rays or microwave.

The polyimide molded product obtained by one of the aforesaid three methods may be formulated into an intraocular lens by, for example, machining processing. That is, a lens is formed by abrading the curved surface in accordance with the required degree. Next, a hole for providing a fixing part is formed by numerical control processing (NC processing) and the fixing part is solvent-welded to the hole by spot heating.

Figure 1:
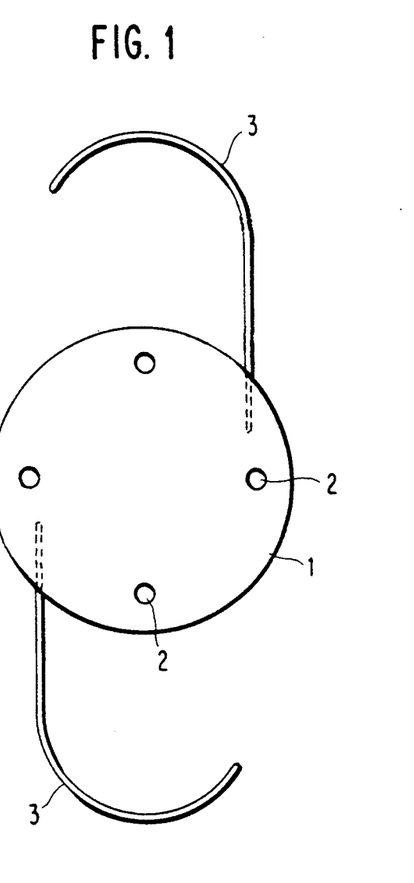
FIG. 1 is a plan view of an intra-ocular lens to be implanted into the posterior chamber of a human eye.
Figure 2:
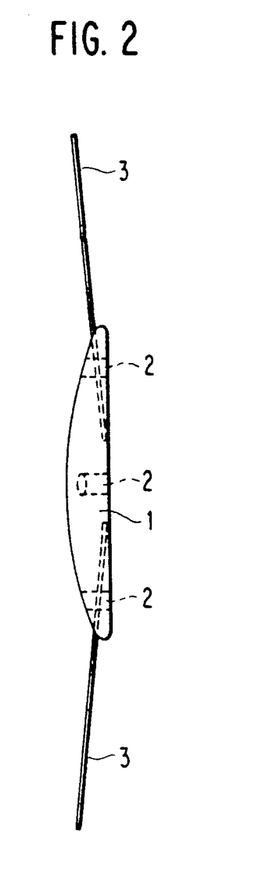
FIG. 2 is a side view of the intra-ocular lens shown in FIG. 1.

FIGS. 1 and 2 show each an example of the intraocular lens thus obtained to be put into the posterior chamber of a human eye. In these figures, 1 is a lens part; 2 is a hole for positioning formed along the peripheral portion of the lens part 1; and 3 is a fixing part for fixing the lens part 1 in the eye.

The form of the aforesaid fixing part 3 may be widely varied if required. Commonly employed examples of the material of the fixing part 3 include polypropylene and polyvinylidene fluoride. In the intra-ocular lens of the present invention, however, the fixing part may be made of either one of these materials or others. It is also possible to use the same colorless and transparent polyimide as the one employed for the lens part as the fixing part.

Figure 3:
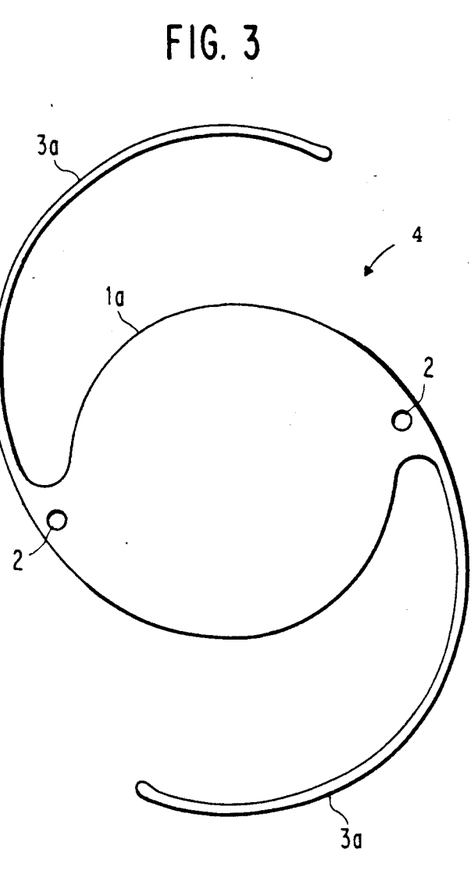
FIG. 3 is a plan view of an intra-ocular lens wherein a lens part and a fixing part are integrally molded.
Figure 4:
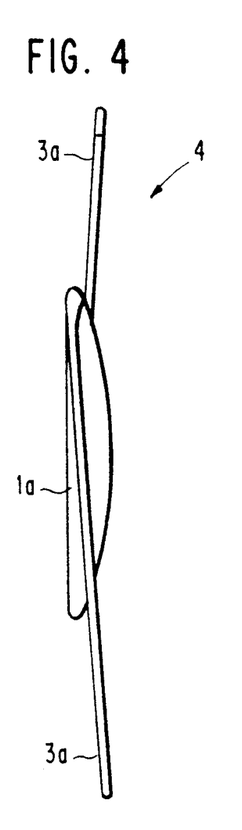
FIG. 4 is a side view of the intra-ocular lens shown in FIG. 3.

In the above case, the lens part and the fixing part are separately formed and then connected together. Alternately, it is possible to integrally mold the lens part and the fixing part. FIGS. 3 and 4 show each an example of such an intra-ocular lens wherein the lens part and the fixing part are integrally molded. In these figures, 1a and 3a respectively indicates a lens part and fixing part which are integrated with each other. In this case, there is no connected part and thus the elimination of the fixing part from the lens part would never occur.

Different from conventional ones comprising aromatic polyimide, the intra-ocular lens thus obtained has an extremely high transparency.

The aforesaid colorless and transparent polyimide to be used in the present invention has a visible ray transmittance (500 nm) of 80% or above and a yellowness index of 30 or less, in the case of a molded film of 50 μm in thickness. Further, the lens part of the intra-ocular lens of the present invention has a total transmittance of visible rays (total ray transmittance) of 60% or above, in the case of a thickness of 1 mm.

The lens part of the intra-ocular lens of the present invention would completely absorb ultraviolet rays and transmits most of visible rays, which means that it is substantially transparent. This may be because the point giving a transmittance of zero (i.e., so-called cut-off point) of the colorless and transparent polyimide in the determination of ultraviolet rays/visible rays spectra resides just in the boundary point (380 nm) between the ultraviolet rays and visible rays regions and the cut-off occurs almost vertically. Some aromatic polyimides other than the colorless and transparent polyimide to be used in the present invention also show a cut-off around 380 nm. In these cases, however, a decrease in the transmittance slowly occurs in a higher wavelength side and thus the total ray transmittance becomes extremely poor. Therefore, it is impossible to apply these aromatic polyimides to intra-ocular lenses.

As described above, the intra-ocular lens of the present invention, wherein the lens part comprises colorless and transparent polyimide obtained by combining a 4,4,'-oxydiphthalic dianhydride with the aforesaid specific aromatic diamino compound, can completely absorb ultraviolet rays within a wavelength region of from 200 to 380 nm and transmit of most of visible rays within a wavelength region of from 380 to 780 nm. Thus this lens part is substantially transparent. When embedded in an eye, therefore, the intraocular lens of the present invention can protect the retina from harmful visible rays and give a sufficient eyesight. Furthermore, the aforesaid colorless and transparent polyimide usually has a small specific gravity of 1.3 to 1.4 and a high refraction index of 1.6 to 1.7, compared with conventional PMMA. Thus the thickness of the intra-ocular lens of the present invention can be reduced by 30 to 50%, compared with a conventional PMMA lens of the same degree. In the case of the intra-ocular lens of the present invention, therefore, the width of the incision for embedding can be reduced and the load upon the eye can be relieved. Furthermore, the possibility of the occurrence of complicating diseases caused by the contact with the cornea can be lowered, which suggests that the intra-ocular lens of the present invention is highly safe. In addition, the lens part of the intra-ocular lens of the present invention is made of the colorless and transparent polyimide which is comparable to conventional aromatic polyimides in thermal resistance. Thus, it can be easily sterilized by the autoclave sterilization method, which makes it possible to reduce the sterilization cost.

The intra-ocular lens of the present invention can be used as an anterior chamber supporting lens, a posterior chamber supporting lens or, in some cases, an iris supporting lens. Thus the present invention involves all of these intra-ocular lenses.

The present invention will be described in more detail by reference to the following Examples and Comparative Examples, but the present invention is not construed as being limited thereto.

EXAMPLES 1 TO 16

By using n,N-dimethylacetamide as a solvent, 1 mole of 4,4,'-oxydiphthalic dianhydride was reacted with each diamino compound as specified in the following Table to thereby give a polyamide acid solution. The concentration of the polyamide acid polymer in the polyamide acid solution was adjusted to 20 % by weight.

This solution was casted onto a glass plate to thereby form a coating. It was then converted into the corresponding imide by heating in a hot air dryer at 120° C. for 60 minutes, at 180° C. for 60 minutes, at 250° C. for 3 hours and at 300° C. for 30 minutes. Thus a polyimide film of 50 μm in thickness was prepared. The infrared absorption spectrum of the polyimide film thus obtained was determined. As a result, no absorption caused by the amide acid but an absorption characteristic to an imide group was observed at 1780 cm$^{-1}$.

The aforesaid polyimide film was punched out with a punch of 38 mm in diameter, and 20 punched films were laminated and subjected to hot press molding at a temperature of 300° C. under a pressure of 1 t/cm$^2$ for 30 minutes. Thus, a polyimide disc molded product of 1 mm in thickness was obtained. In this molded article, the films were completely integrated together so as to give a homogeneous polyimide molded product.

The ultraviolet-visible ray spectrum of the polyimide molded product thus obtained were determined to thereby determine the wavelength at the cut off point thereof. Further, the total ray transmittance, the specific gravity and the refraction index thereof were determined. The following table summarizes the results. Furthermore, a pressure cooker test was performed at 121° C. under 1.2 atmosphere for 24 hours to thereby examine a change in the appearance. The results are also given in the following table.

EXAMPLE 17

By using N,N-dimethylacetamide as a solvent, 1 mole of 4,4,'-oxydiphthalic dianhydride was reacted with 2,2-bis(4-(4-aminophenoxy)phenyl)propane and 4,4,'-diaminodiphenylpropane, which were employed as aromatic diamino compounds at a ratio by mole of 8/2, to thereby give a polyamide acid solution. Then a polyimide film of 50 μm in thickness was prepared in the same manner as the one described in Example 1. Similar to Example 1, the wavelength at the cut off point, the total ray transmittance, the specific gravity and the refraction index of the polyimide film thus obtained were determined. The following table summarizes the results. Furthermore, a pressure cooker test was performed in the same manner as the one described in Example 1 and the results are also given in the table.

COMPARATIVE EXAMPLE 1

By using N-methyl-2-pyrrolidone as a solvent, 1 mole of oxydiphthalic dianhydride was reacted with 1 mole of 4,4,'-diaminodiphenyl ether to thereby give a polyamide acid solution. Then a polyimide film was prepared in the same manner as the one described in Example 1. The infrared spectrum of this film showed no absorption of the amide acid but an absorption of an imide group at 1780 cm$^{-1}$.

Then the polyimide film thus obtained was formulated into a polyimide molded product of 1 mm in thickness in the same manner as the one described in Example 1. This molded product was considerably colored and thus it was impossible to examine whether the films were completely integrated together or not. The wavelength at the cut off point, the total ray transmittance, the specific gravity and the refraction index of this product were determined, similar to Example 1, and the results are summarized in the following table.

EXAMPLE 18

The polyamide acid solution obtained in Example 1 was poured into water and the polyamide acid was reprecipitated. After thoroughly stirring, the solvent was removed and the precipitate was washed with methanol and dried under reduced pressure. Next, the polyamide acid powder thus obtained was heated to 250° C. in a hot air dryer to thereby convert it into the corresponding imide. Then the obtained imide was ground to thereby give a fine powder.

The polyimide powder thus obtained was subjected to hot press molding at a temperature of 300° C. under a pressure of 1 t/cm$^2$ for 30 minutes to thereby give a polyimide molded product of 1 mm in thickness. This molded product, wherein grains were completely integrated together, comprised a homogeneous and transparent polyimide.

Similar to Example 1, the wavelength at the cut off point, the total ray transmittance, the specific gravity and the refraction index of the polyimide molded product thus obtained were determined and the results are summarized in the following table. Similar to Example 1, furthermore, a pressure cooker test was performed and the results are also given in the table.

COMPARATIVE EXAMPLE 2

By using the polyamide acid solution obtained in Comparative Example 1, a polyimide powder was prepared in the same manner as the one described in Example 18.

The polyimide powder thus obtained was formulated into a polyimide molded product of 1 mm in thickness in the same manner as the one described in Example 18. This molded product was considerably colored and, furthermore, the grains therein were not completely integrated together.

Similar to Example 1, the wavelength at the cut off point, the total ray transmittance, the specific gravity and the refraction index of the polyimide molded product thus obtained were determined and the results are summarized in the following table.

EXAMPLE 19

The polyamide acid solution obtained in Example 4 was introduced into a Petri dish and dried in a vacuum dryer under reduced pressure at 25° C. for 24 hours. Then it was treated at 100° C. for 48 hours, at 150° C. for 48 hours and finally at 250° C. for 24 hours while maintaining the reduced pressure. Thus a polyimide molded product of 1.0 mm in thickness was prepared. This molded product comprised a homogeneous and transparent polyimide.

Similar to Example 1, the wavelength at the cut off point, the total ray transmittance, the specific gravity and the refraction index of the polyimide molded product thus obtained were determined and the results are summarized in the following table. Similar to Example 1, furthermore, a pressure cooker test was performed and the results are also given in the table.

COMPARATIVE EXAMPLE 3

By using the polyamide acid solution obtained in Comparative Example 1, a polyimide molded product of 0.8 mm in thickness was prepared in the same manner as the one described in Example 19. This molded product comprised a homogeneous but significantly colored polyimide.

Similar to Example 1, the wavelength at the cut off point, the total ray transmittance, the specific gravity and the refraction index of the polyimide molded product thus obtained were determined and the results are summarized in the following table.

In the following table, 4,4,'-BAPP represents 2,2-bis(4-(4-aminophenoxy)phenyl)propane; 4,4,'-BAPS L represents bis(4-(4-aminophenoxy)phenyl)sulfone; 4,4,'-BAPF represents 2,2-bis(4-(3-aminophenoxy)phenyl)hexafluoropropane; 1,3,4-BAPB represents 1,3-bis(4-aminophenoxy)benzene; 1,4,4-BAPB represents 1,4-bis(4-aminophenoxy)benzene; BAPD represents 4,4,'-bis(4-aminophenoxybiphenyl; 4,4,'-DDP represents 4,4,'-diaminodiphenylpropane; 4,4,'-DDF represents 4,4,-diaminodiphenylhexafluoropropane; 3,4,-DDE represents 3,4,-diaminodiphenyl ether; 4,4,'-DDE represents 4,4,'-diaminodiphenyl ether; 3,3,'-BAPS represents bis(4-(3-aminophenoxy)phenyl)sulfone; 3,3,'-BAPP represents 2,2,-bis(4-(3-aminophenoxy)phenyl)propane; 3,3,'-BAPF represents 2,2-bis(4-(3-aminophenoxy)phenyl)hexafluoropropane; 3,3,'-DDS represents 3,3,'-diaminodiphenylsulfone; 3,3,'-DDP represents 3,3,'-diaminodiphenylpropane; 3,3,'-DDF represents 3,3,'-diaminodiphenylhexafluoropropane; 3,3,'-DDE represents 3,3,'-diaminodiphenyl ether; and 4,4,'-BAPE represents bis(4-(4-aminophenoxy)phenyl) ether.

TABLE

| | Aromatic diamino compound | Wavelength at cut off point (nm) | Total ray transmittance (%) | Specific gravity | Refraction index | Change in appearance after pressure cooker test |
|---|---|---|---|---|---|---|
| Example 1 | 4,4'-BAPP | 387 | 69 | 1.38 | 1.651 | no change |
| Example 2 | 4,4'-BAPS | 395 | 68 | 1.39 | 1.680 | no change |
| Example 3 | 4,4'-BAPF | 383 | 71 | 1.39 | 1.625 | no change |
| Example 4 | 1,3,4-BAPB | 390 | 70 | 1.37 | 1.642 | no change |
| Example 5 | 1,4,4-BAPB | 396 | 68 | 1.35 | 1.668 | no change |
| Example 6 | BAPD | 393 | 67 | 1.41 | 1.673 | no change |
| Example 7 | 4,4'-DDP | 396 | 70 | 1.34 | 1.654 | no change |
| Example 8 | 4,4'-DDF | 382 | 73 | 1.40 | 1.623 | no change |
| Example 9 | 3,4'-DDE | 398 | 66 | 1.36 | 1.665 | no change |
| Example 10 | 3,3'-BAPS | 390 | 70 | 1.39 | 1.660 | no change |
| Example 11 | 3,3'-BAPP | 388 | 71 | 1.35 | 1.650 | no change |
| Example 12 | 3,3'-BAPF | 375 | 74 | 1.42 | 1.619 | no change |
| Example 13 | 3,3'-DDS | 380 | 70 | 1.39 | 1.673 | no change |
| Example 14 | 4,4'-BAPE | 399 | 66 | 1.41 | 1.681 | no change |
| Example 15 | 3,3'-DDF | 372 | 76 | 1.43 | 1.610 | no change |
| Example 16 | 3,3'-DDE | 381 | 71 | 1.39 | 1.660 | no change |
| Example 17 | 4,4'-BAPP/ 4,4'-DDP | 392 | 70 | 1.37 | 1.652 | no change |
| Comparative Example 1 | 4,4'-DDE | 443 | 0.5 | 1.43 | 1.704 | — |
| Example 18 | 4,4'-BAPP | 383 | 70 | 1.40 | 1.654 | no change |
| Comparative Example 2 | 4,4'-DDE | 445 | 0.5 | 1.43 | 1.700 | — |
| Example 19 | 1,3,4-BAPB | 385 | 71 | 1.39 | 1.637 | no change |
| Comparative Example 3 | 4,4'-DDE | 445 | 1.2 | 1.41 | 1.713 | — |

As the results shown in the above table indicate, each product of the present invention shows an extremely high total ray transmittance and a small specific gravity, compared with the conventional products. Further, each product of the present invention shows a wavelength of the cut off point around the boundary position (380 nm) between the ultraviolet rays and visible rays regions, which suggests that it absorbs ultraviolet rays and allows to transmit of most of visible rays.

EXAMPLE 20

By using the polyimide molded product obtained in Example 18, the lens part 1 of FIG. 1 was produced. As the fixing part 3, polyvinylidene fluoride was employed. Thus an intra-ocular lens for rabbit eye was obtained. The intraocular lens thus obtained was embedded in the anterior chamber of a rabbit eye and the effects thereof were monitored for 6 months.

EXAMPLE 21

An intra-ocular lens for rabbit eye was produced by using the polyimide molded product obtained in Example 11 for both of the lens part and the fixing part shown in FIG. 1. The intra-ocular lens thus obtained was embedded in the anterior chamber of a rabbit eye and the effects were monitored for 6 months.

EXAMPLE 22

By using the polyimide molded product obtained in Example 11, an intra-ocular lens 4 for rabbit eye as shown in FIG. 4, wherein the lens part 1a and the fixing part 3a were integrally molded together, was produced. The obtained intra-ocular lens 4 was embedded in the anterior chamber of a rabbit eye and the effects thereof were monitored for 6 months.

As a result, neither any toxicity nor any harmful effect was observed in the aforesaid Examples 20, 21 and 22. When each lens was taken out again and the optical properties thereof were determined, no change was observed, compared with the properties observed prior to the embedding.

While the invention has been described in detail and with reference to specific examples thereof, it will be apparent to one skilled in the art that various changes and modifications can be made therein without departing from the spirit and scope thereof.

What is claimed is:

1. An intra-ocular lens comprising a lens part and a fixing part for fixing said lens part in an eye, said lens part comprising a colorless and transparent polyimide containing at least one of repeating units represented by formulae (I) to (IV):

(I)

(II)

(III)

(IV)

wherein
$X_1$ represents $X_2$ represents

; and $X_3$ represents

2. An intra-ocular lens as claimed in claim 1, wherein said polyimide contains 80% by mole or more of at least one of said repeating units represented by formulae (I) to (IV).

3. An intra-ocular lens as claimed in claim 2, wherein said polyimide contains 95% by mole or more of at least one of said repeating units represented by formulae (I) to (IV).

4. An intra-ocular lens as claimed in claim 1, wherein said lens part and said fixing part are integrated together and comprise said colorless and transparent polyimide containing at least one of the repeating units represented by formulae (I) to (IV).

* * * * *